(12) United States Patent
Duboux et al.

(10) Patent No.: US 11,452,308 B2
(45) Date of Patent: Sep. 27, 2022

(54) METHOD OF SELECTING A PROBIOTIC (71) Applicant: SOCIETE DES PRODUITS NESTLE S.A., Vevey (CH)

(72) Inventors: Stephane Duboux, St-Prex (CH); Marie Noelle Horcajada, Echenevex (FR); Laure Poquet, Servion (CH)

(73) Assignee: Societe des Produits Nestle S.A., Vevey (CH)

( * ) Notice: Subject to any disclaimer, the term of this patent is extended or adjusted under 35 U.S.C. 154(b) by 161 days.

(21) Appl. No.: 16/762,402

(22) PCT Filed: Nov. 8, 2018

(86) PCT No.: PCT/EP2018/080545
§ 371 (c)(1),
(2) Date: May 7, 2020

(87) PCT Pub. No.: WO2019/092066
PCT Pub. Date: May 16, 2019

(65) Prior Publication Data
US 2020/0345050 A1    Nov. 5, 2020

(30) Foreign Application Priority Data

Nov. 8, 2017 (EP) .................... 17200578

(51) Int. Cl.
*C12N 15/09* (2006.01)
*A23L 33/135* (2016.01)
*A61K 31/05* (2006.01)
*C12Q 1/02* (2006.01)
*C12Q 1/44* (2006.01)
*A61K 9/00* (2006.01)

(52) U.S. Cl.
CPC ............ *A23L 33/135* (2016.08); *A61K 31/05* (2013.01); *C12Q 1/02* (2013.01); *C12Q 1/44* (2013.01); *A61K 9/0053* (2013.01); *G01N 2333/924* (2013.01)

(58) Field of Classification Search
CPC ..................................................... C12N 15/09
See application file for complete search history.

(56) References Cited

U.S. PATENT DOCUMENTS 9,132,145 B2    9/2015 Lee-Huang et al.
2008/0014322 A1    1/2008 Ibarra et al.
(Continued)

OTHER PUBLICATIONS

Marino et al., "Role of natural antioxidants and potential use of bergamot in treating rheumatoid arthritis," PharmaNutrition 3:53-59, 2015.*
(Continued)

*Primary Examiner* — Rosanne Kosson
(74) *Attorney, Agent, or Firm* — K&L Gates LLP

(57) ABSTRACT

The present invention relates generally to probiotics, in particular probiotics capable of bio-converting olive polyphenols. The invention relates to a method of selecting a probiotic strain or probiotic strain mixture. Further aspects of the invention include the use of a probiotic strain to increase the bio-efficacy of olive polyphenols and a composition comprising a probiotic strain for use in the potentiation of a therapeutic effect and/or a prophylactic effect of oleuropein.

10 Claims, 2 Drawing Sheets

Oleuropein

Oleuropein aglycon

Hydroxytyrosol acetate
Hydroxytyrosol
Elenolic acid
Elenolic acid (56) References Cited

U.S. PATENT DOCUMENTS

2016/0101125 A1    4/2016  Horcajada et al.
2016/0263139 A1    9/2016  Horcajada et al.

OTHER PUBLICATIONS

Peres Catia et al. "Novel isolates of lactobacilli from fermented Portuguese olive as potential probiotics" LWT—Food Science and Technology, Mar. 10, 2014, vol. 59, No. 1, pp. 234-246, XP028862673.
Santos et al. "Bioconversion of oleuropein to hydroxytyrosol by lactic acid bacteria" World Journal of Microbiology and Biotechnology, Mar. 20, 2012, vol. 28, No. 6, pp. 2435-2440, XP035053735.
Marsilio et al. "Characterisitation of an Oleuropein Degrading Strain of Lactobacillus plantarum. Combined Effects of Compounds Present, in Olive Fermenting Brines (Phenols, Glucose and NaCl) on Bacterial Activity" J Sci Food Agric, Jan. 1, 1998, pp. 520-524, XP055438272.
Peres et al. "Synergy of olive bioactive phytochemicals and probiotic strain in control of *Escherichia coli*" Food Science and Technology, Dec. 1, 2015, vol. 64, No. 2, pp. 938-945, XP055438275.
Miriam et al. "Selection of Lactobacillus plantarums strains to use as starters in fermented table olives: Oleuropeinase activity and phage sensitivity" Food Microbiology, Nov. 28, 2012, vol. 34, No. 1, pp. 81-87, XP028998053.
Marsilio et al. "Progress in Table Olive Debittering: Degradation in vitro of Oleuropein and its Derivatives by Lactobacillus Plantarum" Journal of the American Oil Chemists' Society, Jan. 1, 1996, vol. 73, No. 5, pp. 593,597, XP002060794.

\* cited by examiner

METHOD OF SELECTING A PROBIOTIC

CROSS REFERENCE TO RELATED APPLICATIONS

The present application is a National Stage of International Application No. PCT/EP2018/080545, filed on Nov. 8, 2018, which claims priority to European Patent Application No. 17200578.7, filed on Nov. 8, 2017, the entire contents of which are being incorporated herein by reference.

FIELD OF THE INVENTION

The present invention relates generally to probiotics, in particular probiotics capable of bio-converting olive polyphenols. The invention relates to a method of selecting a probiotic strain or probiotic strain mixture. Further aspects of the invention include the use of a probiotic strain or probiotic strain mixture to increase the efficacy of olive polyphenols and a composition comprising a probiotic strain or probiotic strain mixture for use in the potentiation of a therapeutic effect and/or a prophylactic effect of oleuropein.

BACKGROUND OF THE INVENTION

Oleuropein is a polyphenol found in the fruit, the roots, the trunk and more particularly in the leaves of plants belonging to the Oleaceae family, and especially *Olea europaea*. The present inventors noted that in vitro data generated on chondrocytes metabolism obtained significant positive results with the oleuropein metabolite hydroxytyrosol, which showed higher efficacy compared to oleuropein. Without being bound by theory, based on the literature the present inventors believe that the chemical structure of hydroxytyrosol suggests that hydroxytyrosol has a higher bioavailability than oleuropein. Again without being bound by theory, the present inventors further believe that a portion of a dose of oleuropein can be absorbed as such in the intestinal upper level and another portion can reach the colon where it would mainly be absorbed after bioconversion into hydroxytyrosol and/or an intermediate metabolite such as oleuropein aglycone or hydroxytyrosol acetate.

Enhanced absorption of a metabolite of oleuropein at the colon could increase bioavailability of the oleuropein and thereby potentially increase the efficacy of the oleuropein. In this regard, co-administration of oleuropein with one or more probiotics having a glycosidase activity and/or an esterase activity can increase the presence of this probiotic in the colon to allow the degradation in situ of the oleuropein in order to optimize the absorption and consequent effect of a metabolite thereof.

*Lactobacillus plantarum* strain B21 has been proposed for de-bittering olives [Marsilio et al., J. Sci. Food Agric. 76, 520-524 (1998)] where it has been shown to degrade oleuropein. However, the fermentation process took around 5 days which is far longer than a realistic timeframe for digestion and so *L. plantarum* strain B21 would not provide a suitable probiotic for co-administration with oleuropein to enhance bio-availability and/or bio-efficacy.

There is a clear need in the art to find improved methods for identifying probiotics, in particular probiotics which are capable of increasing the bio-availability and/or bio-efficacy of olive polyphenols such as oleuropein.

Any reference to prior art documents in this specification is not to be considered an admission that such prior art is widely known or forms part of the common general knowledge in the field. As used in this specification, the words "comprises", "comprising", and similar words, are not to be interpreted in an exclusive or exhaustive sense. In other words, they are intended to mean "including, but not limited to".

SUMMARY OF THE INVENTION

An object of the present invention is to improve the state of the art and to provide an improved solution to the problem of identifying probiotics, or at least to provide a useful alternative.

The object of the present invention is achieved by the subject matter of the independent claims. The dependent claims further develop the idea of the present invention.

Accordingly, the present invention provides in a first aspect a method of selecting a probiotic strain or probiotic strain mixture the method comprising the steps of;

a. identifying a probiotic strain having a β-glucosidase encoding gene by in silico analysis and/or β-glucosidase activity by in vitro analysis of a plurality of strains;

b. identifying a probiotic strain having an esterase encoding gene by in silico analysis and/or esterase activity by in vitro analysis of a plurality of strains;

c. fermenting oleuropein with i) a bacterial culture of a probiotic strain identified in step a as having β-glucosidase activity and a probiotic strain identified in step b as having esterase activity, or ii) a bacterial culture of a probiotic strain identified in steps a and b as having both β-glucosidase and esterase activity;

d. identifying whether the metabolites formed during the fermentation of step c include hydroxytyrosol acetate, hydroxytyrosol or elenolic acid;

e. measuring the proportion of oleuropein remaining as a function of fermentation time in step c; and f. selecting a probiotic strain or probiotic strain mixture wherein the probiotic strain or probiotic strain mixture consumes at least 10 wt. % of oleuropein in step c over a time period of less than 24, and wherein the metabolites formed during the fermentation of step c comprise a molecule selected from the group consisting of hydroxytyrosol acetate, hydroxytyrosol and elenolic acid.

In a second aspect, the invention relates to the use of a probiotic strain or probiotic strain mixture selected according to the method of the invention to increase the efficacy of olive polyphenols.

A third aspect of the invention relates to a composition comprising a probiotic strain or probiotic strain mixture selected according to the method of the invention for use in the potentiation of a therapeutic effect and/or a prophylactic effect of oleuropein in an individual.

It has been surprisingly found by the inventors that probiotics or probiotic mixtures selected by the method of the invention were capable of increasing the bio-availability of olive polyphenols such as oleuropein and their efficacy (i.e. their bio-efficacy). The probiotics or probiotic mixtures selected by the method of the invention are capable of converting oleuropein to its metabolites over a timescale that is effective over the timescale of digestion. This allows the probiotics to be effective when co-administered with oleuropein, or taken separately, but within a few hours of each other.

The mechanism of oleuropein absorption is not clear. Nevertheless, oleuropein resists degradation in the upper gastrointestinal tract and the small intestine, and thus at least a portion of a dose of oleuropein will reach the colon. Microflora in the colon can then perform bioconversion on this oleuropein.

Figure 1:
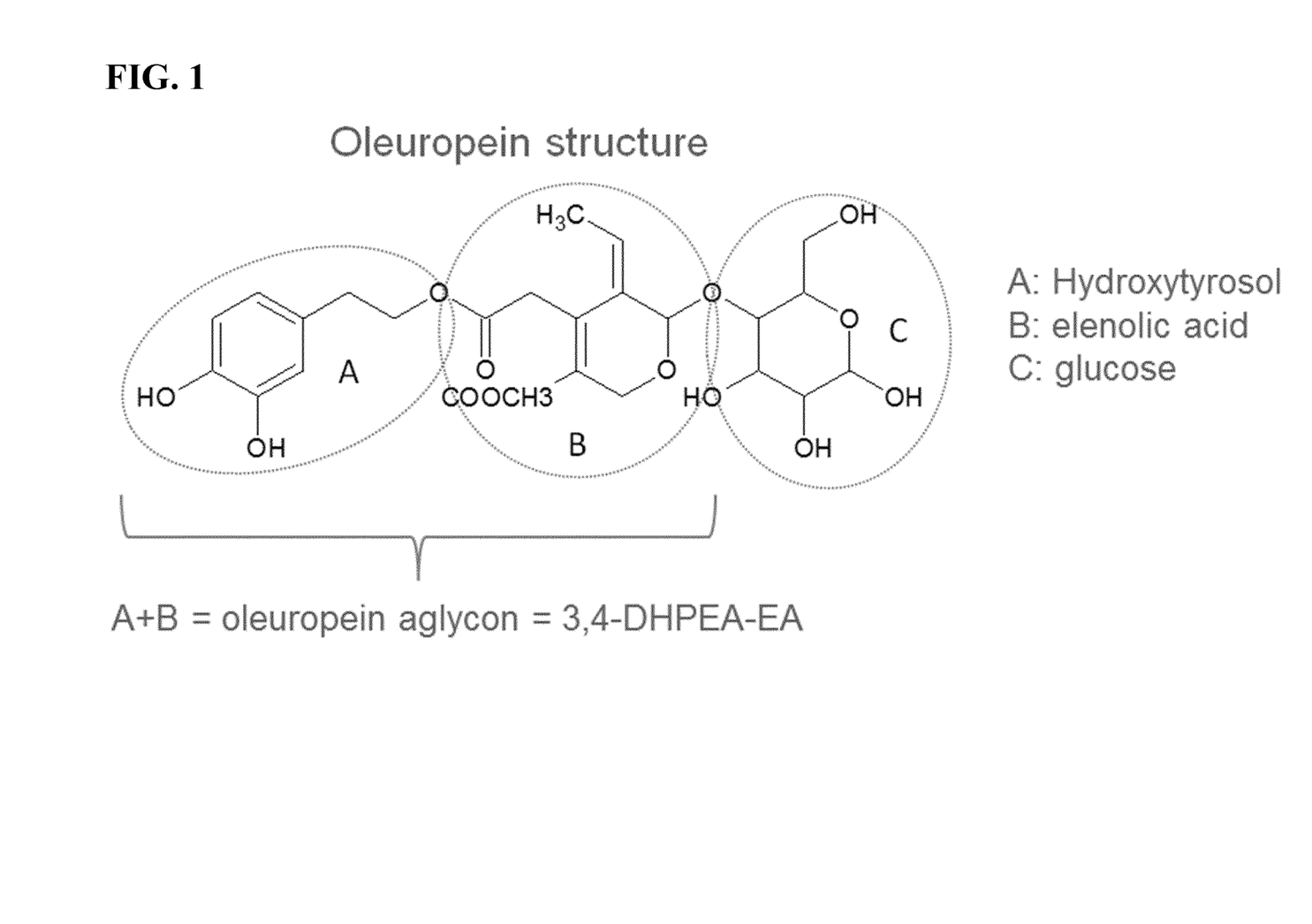
FIG. 1 shows the chemical structure of oleuropein.
Figure 2:
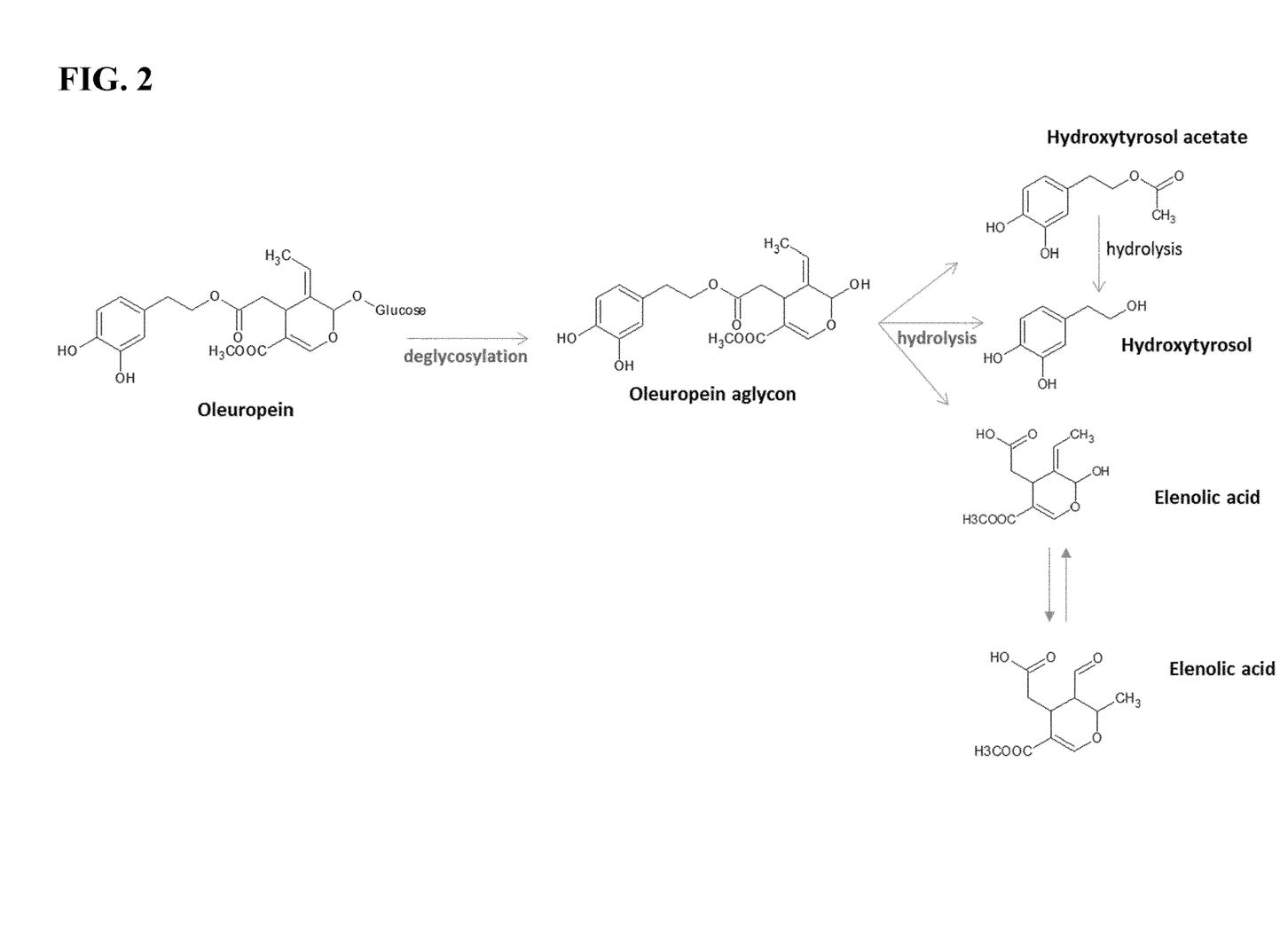
FIG. 2 shows the bioconversion of oleuropein by microflora.

As shown in FIG. 2, deglycosylation converts the oleuropein to oleuropein aglycone (also known as 3,4-dihydroxyphenylethanol-elenolic acid or "3,4-DHPEA-EA"). Then hydrolysis (e.g., by an esterase) can form hydroxytyrosol acetate and/or elenolic acid, and further hydrolysis can form hydroxytyrosol from the hydroxytyrosol acetate.

According to the literature, oleuropein aglycone is 2.2 times less absorbed compared with hydroxytyrosol, but 13.5 times more absorbed than oleuropein. Oleuropein aglycone has a slower clearance from the plasma compared with hydroxytyrosol and oleuropein. Moreover, oleuropein aglycone has an antioxidant activity comparable to that of caffeic acid, oleuropein and hydroxytyrosol.

Hydroxytyrosol absorption is higher than oleuropein and oleuropein aglycone, and hydroxytyrosol acetate absorption is even higher than that of hydroxytyrosol. In this regard, hydroxytyrosol acetate is more soluble in the lipophilic phases than hydroxytyrosol due to the presence of the ester group in hydroxytyrosol acetate. The present inventors believe that this increased lipophilicity suggests that hydroxytyrosol acetate is better absorbed across intestinal epithelial cell monolayers than free hydroxytyrosol.

Oleuropein can be absorbed as such in the upper gastrointestinal tract or can reach the colon were it would mainly be absorbed after bioconversion into oleuropein aglycone, hydroxytyrosol acetate, and/or hydroxytyrosol. However, the proportion of oleuropein not absorbed in the upper gastrointestinal tract and thus reaching the colon for further metabolism after bioconversion is not well defined. Therefore, without being bound by theory, the present inventors believe that enhancing absorption of oleuropein or a derivative thereof in the colon can increase the potential efficacy of the oleuropein following oral intake and thereby increase the bioavailability thereof. Indeed, enhanced absorption of oleuropein or a derivative thereof in the colon could provide efficacy from at least two sites of absorption and the at least two circulating compounds, namely the parent and one or more metabolites (e.g., dual efficacy).

Specifically, co-administration of oleuropein with one or more probiotics selected according to the method of the invention can increase the presence of probiotics in the colon and thus allow the degradation in situ of oleuropein in order to optimize the absorption and consequent effect of oleuropein. For example, a probiotic having β-glycosidase activity, preferably β-glucosidase activity (and preferably not esterase activity) can convert the oleuropein into oleuropein aglycone in the colon. A probiotic having β-glycosidase activity (preferably β-glucosidase activity) and esterase activity can convert the oleuropein into hydroxytyrosol acetate and/or hydroxytyrosol in the colon. Establishing and/or increasing the presence of such microorganisms in the colon can potentiate the effect of oleuropein administration, thereby providing an extended absorption over time with oleuropein (e.g., absorption at two different levels: small intestine, colon), for example absorption that is extended relative to hydroxytyrosol by itself which provides a more acute peak of absorption. With the metabolites being generated faster due to co-adminisration of oleuropein and probiotics selected according to the method of the invention, the onset of their bioavailability may be sooner, leading to a longer overall period of absorption.

DETAILED DESCRIPTION OF THE INVENTION

Consequently the present invention relates in part to a method of selecting a probiotic strain or probiotic strain mixture (for example to increase the bio-efficacy of olive polyphenols) the method comprising the steps of;
  a. identifying a probiotic strain having a β-glucosidase encoding gene by in silico analysis and/or β-glucosidase activity by in vitro analysis of a plurality of strains;
  b. identifying a probiotic strain having an esterase encoding gene by in silico analysis and/or esterase activity by in vitro analysis of a plurality of strains;
  c. fermenting oleuropein with i) a bacterial culture of a probiotic strain identified in step a as having β-glucosidase activity and a probiotic strain identified in step b as having esterase activity, or ii) a bacterial culture of a probiotic strain identified in steps a and b as having both β-glucosidase and esterase activity;
  d. identifying whether the metabolites formed during the fermentation of step c include hydroxytyrosol acetate, hydroxytyrosol or elenolic acid;
  e. measuring the proportion of oleuropein remaining as a function of fermentation time in step c; and
  f. selecting a probiotic strain or probiotic strain mixture wherein the probiotic strain or probiotic strain mixture consumes at least 10 wt. % of oleuropein in step c over a time period of less than 24, and wherein the metabolites formed during the fermentation of step c comprise a molecule selected from the group consisting of hydroxytyrosol acetate, hydroxytyrosol and elenolic acid.

The fermentation in step c may be performed at, or close to, the optimum growth conditions of the probiotic strain, such conditions being readily determined by the skilled person. The fermentation in step c may be performed in the absence of sugars, other than the glucose moiety which is part of the oleuropein molecule.

Identification of a probiotic strain in step a by in silico analysis according to the method of the invention may be performed by providing the genome of the probiotic strain and performing a sequence similarity search for a gene coding for a β-glucosidase enzyme in the genome of the probiotic strain. Identification of a probiotic strain in step b by in silico analysis according to the method of the invention may be performed by providing the genome of the probiotic strain and performing a sequence similarity search for a gene coding for a esterase enzyme in the genome of the probiotic strain. For example, *Lactobacillus johnsonii* NCC 533 was previously demonstrated to contain a gene encoding a cinnamoyl esterase [Lai et al., Appl Environ Microbiol, 75(15): 5018-24 (2009]. The gene Lj1228 may therefore be used as a reference protein to search for other esterase coding genes in probiotic genomes, searching by sequence similarity (BLASTP). A sequence similarity search may also be made at the protein level. For example, for β-glucosidase the sequence of a protein having β-glucosidase activity may be used, taken from a database such as UniProt. An example would be Q5FJD3 from *Lactobacillus acidophilus* NCFM.

Identification of a probiotic strain in steps a and b by in vitro analysis according to the method of the invention may be performed by phenotypic screening. For example a semi-quantitative micro method for the identification of enzymatic activities may be used such as the API ZYM system.

Identification of at least one of the metabolites formed during the fermentation of step c may for example be performed by HPLC analysis.

The proportion of oleuropein remaining as a function of fermentation time in step c may for example be performed by a spectrophotometric method. For example using a wavelength that can distinguish between oleuropein and its metabolites. 300 nm was found by the inventors to be a wavelength where oleuropein concentration could be measured without significant contribution from absorption by hydroxytyrosol.

In an embodiment, the method of the invention further comprises the steps of determining if the probiotic strain or probiotic strain mixture improves the bioavailabiltiy of oleuropein (optionally determining the effect of the carrier matrix), assessing in vitro efficacy using primary chondrocyte and osteoblast cultures, and/or using a clinical trial investigating the effect of oleuropein and the probiotic strain on health outcomes for example bone and joint health outcomes.

In a further aspect, the probiotic strain or probiotic strain mixture selected according to the method of the invention may be used to increase the efficacy (for example the bio-efficacy) of olive polyphenols such as oleuropein. For example, the probiotic strain or probiotic strain mixture selected according to the method of the invention may act on oleuropein to form a metabolite selected from the group consisting of oleuropein aglycone, hydroxytyrosol acetate, hydroxytyrosol and mixtures thereof. The oleuropein and the oleuropein metabolite provide the therapeutic effect and/or the prophylactic effect for a longer duration than would be obtained by administration of the oleuropein or its metabolites alone. The efficacy of olive polyphenols may be increased following oral intake thereof, by increasing the bioavailability of oleuropein through enhancing its absorption at the colon and thus providing efficacy from at least two sites of absorption and at least two circulating compounds, namely the parent compound and one or more metabolites (e.g., dual efficacy). The invention may provide a composition comprising a probiotic strain or probiotic strain mixture selected according to the method of the invention for use in increasing the efficacy (for example the bio-efficacy) of olive polyphenols such as oleuropein.

Advantageously, the probiotic strain or probiotic strain mixture selected according to the method of the invention may perform bioconversion on the portion of oleuropein that reaches the colon after the partial absorption of oleuropein in the small intestine; higher absorption of 3,4-dihydroxyphenolethanol-elenolic acid (also known as oleuropein aglycone and 3,4-DHPEA-EA) and/or hydroxytyrosol and/or hydroxytyrosol acetate is expected in the colon.

A further advantage of the probiotic strain or probiotic strain mixture selected according to the method of the invention is to providing a longer duration of the therapeutic effect of a dose of oleuropein, possibly by providing an extended absorption over time in which the oleuropein or a metabolite thereof is absorbed at two different levels: small intestine, and colon.

A still further advantage of one or more embodiments provided by the present disclosure is to decrease the dose of oleuropein intake while achieving the same efficacy.

In an embodiment, the probiotic or probiotic strain mixture is comprised within a food or beverage composition further comprising olive polyphenols (for example oleuropein). In a further embodiment, the probiotic or probiotic strain mixture is comprised within a food or beverage composition to be consumed sequentially with olive polyphenols (such as oleuropein).

The dietary benefits of olive polyphenols are enjoyed by healthy individuals. Olives have strong consumer acceptance as a healthy food. Generating olive polyphenol metabolites (for example in foods) is beneficial to healthy individuals, for example when the metabolites provide enhanced bio-availability and efficacy of the olive polyphenols. The probiotic strain or probiotic strain mixture selected according to the method of the invention may be used non-therapeutically to increase the efficacy of olive polyphenols such as oleuropein.

The invention further provides the use of a probiotic strain or probiotic strain mixture selected according to the method of the invention to potentiate a therapeutic effect and/or a prophylactic effect of olive polyphenols such as oleuropein in an individual.

An advantage of one or more embodiments provided by the present disclosure is mobility in aging, frail or pre-frail individuals, for example such individuals who are recovering from rehabilitation or at risk of sarcopenia, and particularly bone and joint benefits in such individuals.

Another advantage of one or more embodiments provided by the present disclosure is to treat or prevent osteopenia (mild loss of bone mass), promote bone growth in young individuals, and/or treat or prevent disorders linked with an unbalanced ratio between bone formation and bone resorption.

Yet another advantage of one or more embodiments provided by the present disclosure is to stimulate bone formation or inhibit bone resorption in a subject suffering from osteoporosis, osteolysis adjacent a prosthesis, periodontal disease, osteoarthritis and/or osteopenia.

Still another advantage of one or more embodiments provided by the present disclosure is to enhance bone formation and/or cartilage anabolism; prevent or treat cartilage breakdown; and/or limit synovitis and the subsequent articular cartilage degradation (osteoarthritis) during aging.

Still another advantage of one or more embodiments provided by the present disclosure is to boost the microflora of an individual, for example an elderly individual.

An aspect of the invention provides a composition comprising a probiotic strain or probiotic strain mixture selected according to the method of the invention for use in the potentiation of a therapeutic effect and/or a prophylactic effect of olive polyphenols such as oleuropein in an individual. In an embodiment the probiotic strain or probiotic strain mixture forms an oleuropein metabolite selected from the group consisting of oleuropein aglycone, hydroxytyrosol acetate, hydroxytyrosol and mixtures thereof. The oleuropein and the oleuropein metabolite may provide a therapeutic effect and/or a prophylactic effect for a longer duration than would be obtained by administration of the oleuropein metabolite by itself. The composition may be administered in an effective amount. The composition may further comprise olive polyphenols, for example oleuropein.

In this regard, "co-administration" of olive polyphenols (for example oleuropein) and a probiotic or probiotic mixture selected according to the method of the invention means that the probiotic or probiotic mixture is administered to an individual who has consumed olive polyphenols (for example oleuropein) and/or will consume olive polyphenols and does not necessarily mean that they are administered at the same time in the same composition. Although concurrent administration is indeed preferred, the present disclosure is not limited to this embodiment. If the olive polyphenols (for example oleuropein) and probiotic or probiotic mixture are comprised within the same composition the oleuropein may be isolated from the probiotics to prevent fermentation of the olive polyphenols on storage. For example, the probiotics may be encapsulated separately from the olive polyphenols. Preferably the probiotic or probiotic mixture only reacts with the olive polyphenols after administration, for example in the digestive tract of the individual.

In an embodiment, the olive polyphenols (for example oleuropein) and the probiotic can be administered sequentially in separate compositions. The term "sequentially" means that the olive polyphenols (for example oleuropein) and the probiotic strain or probiotic strain mixture are administered in a successive manner such that the olive polyphenols (for example oleuropein) are administered at a first time without the probiotic strain or probiotic strain mixture, and the probiotic strain or probiotic strain mixture is administered at a second time subsequent to the first time without the olive polyphenols (for example oleuropein). The time between sequential administrations may be, for example, one or several seconds, minutes or hours in the same day; one or several days or weeks in the same month; or one or several months in the same year. The order of sequential administration may be reversed.

The therapeutic effect and/or prophylactic effect of the composition according to the invention may be selected from the group consisting of the treatment or prevention of impaired mobility in an older adult (for example an elderly individual); the stimulation of bone formation and/or inhibiting bone resorption in an individual having a condition comprising an imbalance between bone formation and bone resorption; treatment or prevention of synovitis; treatment or prevention of articular cartilage degradation subsequent to synovitis in an individual having or recovering from synovitis; and treatment or prevention of cartilage breakdown.

In an embodiment the therapeutic effect and/or a prophylactic effect is the treatment or prevention of impaired mobility in an older adult and the older adult has a condition selected from the group consisting of frailty, pre-frailty, sarcopenia, recovering from sarcopenia, osteoporosis, osteoarthritis, malnutrition, at risk of malnutrition, undergoing rehabilitation, scheduled to undergo rehabilitation within the next year, and combinations thereof.

In a further embodiment the therapeutic effect and/or a prophylactic effect is the stimulation of bone formation and/or inhibiting bone resorption in an individual having a condition comprising an imbalance between bone formation and bone resorption and the condition is selected from the group consisting of osteoporosis, Paget's disease, osteolysis adjacent a prosthesis, a metastatic bone disease, hyperthyroidism, hypercalcemia due to a cancer, multiple myelomas, a periodontal disease, osteoarthritis, osteopenia, a bone deficit resulting from a fracture, fracture healing, and combinations thereof.

In a still further embodiment the therapeutic effect and/or a prophylactic effect is the treatment or prevention of synovitis and the synovitis is associated with a condition selected from the group consisting of lupus, gout, rheumatoid arthritis, osteoarthritis, osteochondritis disease, osteoarthrosis and combinations thereof.

In an embodiment, the composition is administered to the individual for a time period of at least one month; preferably at least two months, more preferably at least three, four, five or six months; most preferably for at least one year. During the time period, the composition can be administered to the individual at least one day per week; preferably at least two days per week, more preferably at least three, four, five or six days per week; most preferably seven days per week. The composition can be administered in a single dose per day or in multiple separate doses per day.

In some embodiments, the composition is used in one of the methods disclosed by U.S. Patent App. Publ. Nos. 2016/0045519 and 2016/0120891 and International Patent App. Publ. No. WO 2015/055468, the entireties of which are incorporated herein by reference.

The effective amount of the composition varies with the particular composition, the age and condition of the recipient, and the particular disorder or disease being treated. Nevertheless, in a general embodiment, the composition can be administered to the individual in an amount that provides $10^5$ to $10^{12}$ colony forming units (cfu) of the probiotic strain or probiotic strain mixture per day, preferably from $10^7$ to $10^{11}$ cfu of the probiotic strain or probiotic strain mixture per day. In an embodiment where the composition comprises oleuropein, the composition can be administered to the individual in an amount that provides 0.01 mg to 2 g of the oleuropein per day, preferably from 0.1 mg to 1 g of the oleuropein per day, and more preferably from 1 mg to 200 mg of the oleuropein per day.

In an embodiment, at least a portion of the oleuropein is obtained by extraction, e.g., by extraction from a plant such as a plant belonging to the Oleaceae family, preferably one or more of the stems, the leaves, the fruits or the stones of a plant belonging to the Oleaceae family such as *Olea europaea* (olive tree), a plant of genus *Ligustrum*, a plant of genus *Syringa*, a plant of genus *Fraximus*, a plant of genus *Jasminum* and a plant of genus *Osmanthus*. Additionally or alternatively, at least a portion of the oleuropein can be obtained by chemical synthesis.

The composition can comprise an effective amount of the combination of the oleuropein and the probiotic or probiotic mixture. For example, a single serving or dose of the composition can comprise the effective amount, and a package can contain one or more of the servings or dose.

The composition can comprise a food additive selected from the group consisting of acidulants, thickeners, buffers or agents for pH adjustment, chelating agents, colorants, emulsifiers, excipients, flavor agents, minerals, osmotic agents, a pharmaceutically acceptable carrier, preservatives, stabilizers, sugars, sweeteners, texturizers, vitamins, minerals and combinations thereof.

The composition can comprise an additional ingredient for bone quality, for example protein, vitamin C, vitamin D, vitamin K2, calcium, phosphorus, magnesium, zinc, hesperidin (flavanone), or combinations thereof. The composition can comprise an additional for joint quality comprising at least one ingredient for short-term joint quality, for example, glucosamine (e.g., glucosamine sulfate), chondroitin (e.g., chondroitin sulfate), hyaluronic acid (e.g., a rooster comb extract rich in hyaluronic acid) or combinations thereof (preferably at least hyaluronic acid), and/or at least one ingredient for long-term joint quality, for example vitamin C, another polyphenol (e.g., curcumin, quercetin and/or rutin), omega-3 fatty acids, or combinations thereof. Non-limiting examples of other suitable additional ingredients for joint quality include collagen, hydrolyzed collagen, *Boswellia serrata*, rose hip, and combinations thereof.

The protein can be whey, e.g., native whey, intact unhydrolyzed whey, whey protein concentrate, whey protein isolate, acid whey, sweet whey, modified sweet whey (sweet whey from which the caseino-glycomacropeptide has been removed), a fraction of whey protein, or whey protein hydrolysate; casein; a vegetable protein such as soy protein;

and combinations thereof. The casein may be provided in free form or in the form of a salt, for example, a sodium salt, a calcium salt or a potassium salt. Although the protein can comprise vegetable protein, in some embodiments the composition is gluten-free.

The protein may be extensively hydrolyzed protein hydrolysates prepared from acid or enzyme treated animal and vegetable proteins, such as casein hydrolysate, whey hydrolysate, casein/whey hydrolysate, soy hydrolysate, and mixtures thereof. "Extensively hydrolyzed" protein hydrolysates means that the intact protein is hydrolyzed into peptide fragments in which a majority of the peptide fragments have a molecular weight less than 1,000 Daltons, preferably at least about 75% and most preferably at least about 95% of the peptide fragments having a molecular weight less than about 1,000 Daltons. Free amino acids and synthetic short peptide chains may be substituted for or added to the protein hydrolysates.

In an embodiment, the protein comprises whey protein micelles as described in U.S. Patent App. Pub. No. 2009/0035437 and its counterpart EP1839492A1 and as further characterized in C. Schmitt et al., Soft Matter 6:4876-4884 (2010) where they are referred to as whey protein microgels (WPM). Particularly, whey protein micelles are the micelles comprised in the whey protein micelles concentrate obtained by the process as disclosed in U.S. Patent App. Pub. No. 2009/0035437 and its counterpart EP1839492A1. Therein, the process for the production of whey protein micelles concentrate comprises the steps of: a) adjusting the pH of a whey protein aqueous solution to a value between 3.0 and 8.0; b) subjecting the aqueous solution to a temperature between 80 and 98° C.; and c) concentrating the dispersion obtained in step b). Thereby, the micelles produced have an extremely sharp size distribution, such that more than 80% of the micelles produced have a size smaller than 1 micron in diameter and preferably are between 100 nm and 900 nm in size. The whey protein micelles can be in liquid concentrate or in powder form. Importantly, the basic micelle structure of the whey proteins is conserved, whether in the liquid concentrate form, the powder form, or reconstituted from the powder, for example in water. The whey protein micelles are physically stable in dispersion, as a powder as well as during spray-drying or freeze-drying.

Non-limiting examples of suitable carbohydrates include starch, sucrose, lactose, glucose, fructose, corn syrup solids, maltodextrin, modified starch, amylose starch, tapioca starch, corn starch, xylitol, sorbitol or combinations thereof. Non-limiting examples of suitable lipids include vegetable fat (such as olive oil, corn oil, sunflower oil, high-oleic sunflower, rapeseed oil, canola oil, hazelnut oil, soy oil, palm oil, coconut oil, blackcurrant seed oil, borage oil, lecithins, and the like), animal fats (such as milk fat), or combinations thereof. The source of fat may also be less refined versions of these fats (e.g., olive oil for polyphenol content).

The composition can be in any oral nutritional form, e.g. as a health drink, as a ready-made drink, optionally as a soft drink, including juices, milk-shake, yogurt drink, smoothie or soy-based drink; in a nutritional supplement; in a food bar; or dispersed in foods of any sort, such as baked products, cereal bars, dairy bars, snack-foods, soups, breakfast cereals, muesli, candies, tabs, cookies, biscuits, crackers (such as rice crackers), and dairy products. The composition may be a pet care product, for example for a companion animal.

The composition may be in the form of tablets, capsules, pastilles or a liquid, for example. The composition may further contain protective hydrocolloids (such as gums, proteins, modified starches), binders, film forming agents, encapsulating agents/materials, wall/shell materials, matrix compounds, coatings, emulsifiers, surface active agents, solubilizing agents (oils, fats, waxes, lecithins or the like), adsorbents, carriers, fillers, co-compounds, dispersing agents, wetting agents, processing aids (solvents), flowing agents, taste masking agents, weighting agents, jellifying agents and gel forming agents.

The composition according to the invention may be a composition for oral administration.

Definitions

Some definitions are provided hereafter. Nevertheless, definitions may be located elsewhere in the specification, and the above header "Definitions" does not mean that such disclosures in the "Embodiments" section are not definitions.

Probiotics are micro-organisms that when administered in adequate amounts confer health benefits to the host. For example, the probiotics according to the present invention may belong to the *Lactobacillus, Bifidobacteria, Lactococcus* or *Streptococcus* genus, for example *Lactobacillus gasseri, Lactobacillus acidophilus, Lactobacillus salivarius, Lactobacillus rhamnosus, Lactobacillus paracasei, Lactobacillus casei, Lactobacillus johnsonii, Lactobacillus plantarum, Lactobacillus fermentum, Lactobacillus lactis, Lactobacillus delbrueckii, Lactobacillus helveticus, Lactobacillus brevis, Lactococcus lactis, Streptococcus salivarius, Streptococcus thermophilus, Bifidobacterium lactis, Bifidobacterium animalis, Bifidobacterium longum, Bifidobacterium breve, Bifidobacterium infantis, Bifidobacterium adolescentis, Bifidobacterium pseudocatenulatum* or mixtures thereof. For further example the probiotic may be selected from the group consisting of *Lactobacillus gasseri, Lactobacillus acidophilus, Lactobacillus salivarius, Lactobacillus rhamnosus, Lactobacillus johnsonii, Lactobacillus fermentum, Lactobacillus lactis, Lactobacillus delbrueckii, Lactobacillus helveticus, Lactobacillus brevis, Lactococcus lactis, Streptococcus salivarius, Streptococcus thermophilus, Bifidobacterium lactis, Bifidobacterium animalis, Bifidobacterium longum, Bifidobacterium breve, Bifidobacterium infantis, Bifidobacterium adolescentis, Bifidobacterium pseudocatenulatum* or mixtures thereof.

All percentages expressed herein are by weight of the total weight of the composition unless expressed otherwise. As used herein, "about," "approximately" and "substantially" are understood to refer to numbers in a range of numerals, for example the range of −10% to +10% of the referenced number, preferably −5% to +5% of the referenced number, more preferably −1% to +1% of the referenced number, most preferably −0.1% to +0.1% of the referenced number. All numerical ranges herein should be understood to include all integers, whole or fractions, within the range. Moreover, these numerical ranges should be construed as providing support for a claim directed to any number or subset of numbers in that range. For example, a disclosure of from 1 to 10 should be construed as supporting a range of from 1 to 8, from 3 to 7, from 1 to 9, from 3.6 to 4.6, from 3.5 to 9.9, and so forth.

As used in this disclosure and the appended claims, the singular forms "a," "an" and "the" include plural referents unless the context clearly dictates otherwise. Thus, for example, reference to "a component" or "the component" includes two or more components.

The words "comprise," "comprises" and "comprising" are to be interpreted inclusively rather than exclusively. Likewise, the terms "include," "including" and "or" should all be construed to be inclusive, unless such a construction is clearly prohibited from the context. Nevertheless, the compositions disclosed herein may lack any element that is not specifically disclosed herein. Thus, a disclosure of an embodiment using the term "comprising" includes a disclosure of embodiments "consisting essentially of" and "consisting of" the components identified. A composition "consisting essentially of" contains at least 50 wt. % of the referenced components, preferably at least 75 wt. % of the referenced components, more preferably at least 85 wt. % of the referenced components, most preferably at least 95 wt. % of the referenced components.

The term "and/or" used in the context of "X and/or Y" should be interpreted as "X," or "Y," or "X and Y." Where used herein, the terms "example" and "such as," particularly when followed by a listing of terms, are merely exemplary and illustrative and should not be deemed to be exclusive or comprehensive. As used herein, "associated with" and "linked with" mean occurring concurrently, preferably means caused by the same underlying condition, and most preferably means that one of the identified conditions is caused by the other identified condition.

The terms "food," "food product" and "food composition" mean a product or composition that is intended for ingestion by an individual such as a human and provides at least one nutrient to the individual. The compositions of the present disclosure, including the many embodiments described herein, can comprise, consist of, or consist essentially of the elements disclosed herein, as well as any additional or optional ingredients, components, or elements described herein or otherwise useful in a diet.

In the context of the present invention, the term individuals is not limited to humans. Individuals may for example be humans, livestock or companion animals.

"Prevention" includes reduction of risk and/or severity of a condition or disorder. The terms "treatment," "treat" and "to alleviate" include both prophylactic or preventive treatment (that prevent and/or slow the development of a targeted pathologic condition or disorder) and curative, therapeutic or disease-modifying treatment, including therapeutic measures that cure, slow down, lessen symptoms of, and/or halt progression of a diagnosed pathologic condition or disorder; and treatment of patients at risk of contracting a disease or suspected to have contracted a disease, as well as patients who are ill or have been diagnosed as suffering from a disease or medical condition. The term does not necessarily imply that a subject is treated until total recovery. The terms "treatment" and "treat" also refer to the maintenance and/or promotion of health in an individual not suffering from a disease but who may be susceptible to the development of an unhealthy condition. The terms "treatment," "treat" and "to alleviate" are also intended to include the potentiation or otherwise enhancement of one or more primary prophylactic or therapeutic measure. The terms "treatment," "treat" and "to alleviate" are further intended to include the dietary management of a disease or condition or the dietary management for prophylaxis or prevention a disease or condition. A treatment can be patient- or doctor-related.

The term "elderly" in the context of a human means an age from birth of at least 60 years, preferably above 63 years, more preferably above 65 years, and most preferably above 70 years. The term "older adult" in the context of a human means an age from birth of at least 45 years, preferably above 50 years, more preferably above 55 years, and includes elderly individuals.

"Sarcopenia" is defined as the age-associated loss of muscle mass and functionality (including muscle strength and gait speed).

As used herein, "frailty" is defined as a clinically recognizable state of increased vulnerability resulting from aging-associated decline in reserve and function across multiple physiologic systems such that the ability to cope with every-day or acute stressors is compromised. In the absence of an established quantitative standard, frailty has been operationally defined by Fried et al. as meeting three out of five phenotypic criteria indicating compromised energetics: (1) weakness (grip strength in the lowest 20% of population at baseline, adjusted for gender and body mass index), (2) poor endurance and energy (self-reported exhaustion associated with VO2 max), (3) slowness (lowest 20% of population at baseline, based on time to walk 15 feet, adjusting for gender and standing height), (4) low physical activity (weighted score of kilocalories expended per week at baseline, lowest quintile of physical activity identified for each gender; e.g., less than 383 kcal/week for males and less than 270 kcal/week for females), and/or unintentional weight loss (10 lbs. in past year). Fried L P, Tangen C M, Walston J, et al., "Frailty in older adults: evidence for a phenotype." J. Gerontol. A. Biol. Sci. Med. Sci. 56(3):M146-M156 (2001). A pre-frail stage, in which one or two of these criteria are present, identifies a high risk of progressing to frailty.

As used herein, an "effective amount" is an amount that prevents a deficiency, treats a disease or medical condition in an individual or, more generally, reduces symptoms, manages progression of the diseases or provides a nutritional, physiological, or medical benefit to the individual. Amounts effective for this purpose will depend on a number of factors known to those of skill in the art such as the severity of the disorder and the weight and general state of the individual. In prophylactic applications, compositions according to the invention are administered to an individual susceptible to or otherwise at risk of a particular disorder in an amount that is sufficient to at least partially reduce the risk of developing a disorder. Such an amount is defined to be an effective amount. Again, the precise amounts depend on a number of patient specific factors such as the individual's state of health and weight. The relative terms "improved," "increased," "enhanced" and the like refer to the effects of the composition disclosed herein, namely a composition comprising the probiotic strain or probiotic strain mixture, relative to a composition lacking the probiotic strain or probiotic strain mixture but otherwise identical.

Those skilled in the art will understand that they can freely combine all features of the present invention disclosed herein. In particular, features described for the product of the present invention may be combined with the method of the present invention and vice versa. Further, features described for different embodiments of the present invention may be combined. Where known equivalents exist to specific features, such equivalents are incorporated as if specifically referred to in this specification.

Further advantages and features of the present invention are apparent from the figures.

The invention claimed is:

1. A method for the potentiation of at least one effect of oleuropein in an individual in need of at least one effect selected from the group consisting of a therapeutic effect against a condition, a reduction of risk of a condition, a reduction of severity of a condition, and/or a prophylactic effect of oleuropein in the individual, wherein the condition is selected from the group consisting of:
(i) osteoporosis, Paget's disease, osteolysis adjacent a prosthesis, a metastatic bone disease, hyperthyroidism, hypercalcemia due to a cancer, multiple myelomas, a periodontal disease, osteoarthritis, osteopenia, a bone deficit resulting from a fracture, fracture healing, and combinations thereof; or
(ii) lupus, gout, rheumatoid arthritis, osteoarthritis, osteochondritis disease, osteoarthrosis and combinations thereof,
the method comprising co-administration of therapeutically effective amounts of:
(a) a probiotic microorganism or a mixture of probiotic microorganisms, wherein the microorganism or microorganisms comprise a gene encoding β-glucosidase and a gene encoding an esterase that yields hydroxytyrosol acetate, hydroxytyrosol or elenolic acid as an esterase reaction product; and
(b) oleuropein, to the individual in need thereof.

2. The method according to claim 1, wherein the probiotic strain or probiotic strain mixture forms an oleuropein metabolite selected from the group consisting of oleuropein aglycone, hydroxytyrosol acetate, hydroxytyrosol and mixtures thereof.

3. The method according to claim 1, wherein the composition comprises olive polyphenols.

4. The method according to claim 1, wherein the therapeutic effect and/or a prophylactic effect is selected from the group consisting of the treatment of impaired mobility in an older adult; the stimulation of bone formation and/or inhibiting bone resorption in an individual having a condition comprising an imbalance between bone formation and bone resorption; treatment of synovitis; treatment of articular cartilage degradation subsequent to synovitis in an individual having or recovering from synovitis; and treatment of cartilage breakdown.

5. The method according to claim 4, wherein the therapeutic effect and/or the prophylactic effect is the treatment of impaired mobility in an older adult and the older adult has a condition selected from the group consisting of frailty, pre-frailty, sarcopenia, recovery from sarcopenia, osteoporosis, osteoarthritis, malnutrition, a risk of malnutrition, undergoing rehabilitation, scheduled to undergo rehabilitation within the next year, and combinations thereof.

6. The method according to claim 4, wherein the therapeutic effect and/or the prophylactic effect is the stimulation of bone formation and/or inhibiting bone resorption in an individual having a condition comprising an imbalance between bone formation and bone resorption, wherein the condition is selected from the group consisting of osteoporosis, Paget's disease, osteolysis adjacent a prosthesis, a metastatic bone disease, hyperthyroidism, hypercalcemia due to a cancer, multiple myelomas, a periodontal disease, osteoarthritis, osteopenia, a bone deficit resulting from a fracture, fracture healing, and combinations thereof.

7. The method according to claim 4, wherein the therapeutic effect and/or a prophylactic effect is the treatment of synovitis and wherein the synovitis is associated with a condition selected from the group consisting of lupus, gout, rheumatoid arthritis, osteoarthritis, osteochondritis disease, osteoarthrosis and combinations thereof.

8. The method according to claim 1, wherein the composition is a composition for oral administration.

9. The method according to claim 8, wherein the composition is a food or beverage product.

10. The method according to claim 9, wherein the composition comprises a component selected from the group consisting of protein, carbohydrate, fat and combinations thereof.

* * * * *